(12) United States Patent
Chen et al.

(10) Patent No.: US 6,174,548 B1
(45) Date of Patent: Jan. 16, 2001

(54) OMEPRAZOLE FORMULATION

(75) Inventors: Chih-Ming Chen, Davie; Joseph Chou, Coral Springs; Unchalee Kositprapa, Fort Lauderdale, all of FL (US)

(73) Assignee: Andrx Pharmaceuticals, Inc., Fort Lauderdale, FL (US)

( * ) Notice: Under 35 U.S.C. 154(b), the term of this patent shall be extended for 0 days.

(21) Appl. No.: 09/143,167

(22) Filed: Aug. 28, 1998

(51) Int. Cl.$^7$ .............................. A61K 9/28; A61K 9/30; A61K 9/42; A61K 9/36
(52) U.S. Cl. ................. 424/474; 424/475; 424/476; 424/480
(58) Field of Search .................. 424/475, 480, 424/20, 474, 451, 408, 476

(56) References Cited

U.S. PATENT DOCUMENTS

| | | |
|---|---|---|
| 4,045,563 | 8/1977 | Berntsson et al. . |
| 4,045,564 | 8/1977 | Berntsson et al. . |
| 4,182,766 | 1/1980 | Krassó et al. . |
| 4,255,431 | 3/1981 | Junggren et al. . |
| 4,337,257 | 6/1982 | Junggren et al. . |
| 4,359,465 | 11/1982 | Ruwart . |
| 4,432,966 | 2/1984 | Zeitoun et al. . |
| 4,508,905 | 4/1985 | Junggren et al. . |
| 4,544,750 | 10/1985 | Brändström et al. . |
| 4,572,833 * | 2/1986 | Pedersen et al. ............ 424/20 |
| 4,620,008 | 10/1986 | Brändström et al. . |
| 4,636,499 | 1/1987 | Brändström et al. . |
| 4,686,230 | 8/1987 | Rainer et al. . |
| 4,738,974 * | 4/1988 | Brandstrom ............ 514/338 |
| 4,786,505 * | 11/1988 | Lovgren et al. ........... 424/468 |
| 4,840,799 | 6/1989 | Appeigren et al. . |
| 4,853,230 | 8/1989 | Lovgren et al. . |
| 5,045,321 | 9/1991 | Makino et al. . |
| 5,093,132 | 3/1992 | Makino et al. . |
| 5,093,342 | 3/1992 | Tomoi et al. . |
| 5,178,867 | 1/1993 | Guittard et al. . |
| 5,204,118 | 4/1993 | Goldman et al. . |
| 5,219,870 * | 6/1993 | Kim ................ 514/338 |
| 5,244,670 | 9/1993 | Upson et al. . |
| 5,288,506 | 2/1994 | Spickett et al. . |
| 5,304,540 | 4/1994 | Blackburn et al. . |
| 5,330,982 | 7/1994 | Tyers . |
| 5,352,688 | 10/1994 | Kaminski . |
| 5,362,424 | 11/1994 | Lee et al. . |
| 5,385,739 * | 1/1995 | Debregeas et al. ........... 424/494 |
| 5,389,664 | 2/1995 | Biale et al. . |
| 5,399,700 | 3/1995 | Min et al. . |
| 5,417,980 | 5/1995 | Goldman et al. . |
| 5,433,959 | 7/1995 | Makino et al. . |
| 5,508,041 | 4/1996 | Lee et al. . |
| 5,518,730 | 5/1996 | Fuisz . |
| 5,599,794 | 2/1997 | Eek et al. . |
| 5,620,964 | 4/1997 | Roth et al. . |
| 5,622,717 | 4/1997 | Fuisz . |
| 5,637,320 | 6/1997 | Bourke et al. . |
| 5,639,478 | 6/1997 | Makino et al. . |
| 5,693,818 | 12/1997 | Von Unge . |
| 5,753,265 * | 5/1998 | Bergstrand et al. ............ 424/474 |
| 5,846,562 * | 12/1998 | Yanai et al. ............ 424/451 |

FOREIGN PATENT DOCUMENTS

| | | |
|---|---|---|
| 1127158 | 7/1982 | (CA) . |
| 1129417 | 8/1982 | (CA) . |
| 1234118 | 3/1988 | (CA) . |
| 1263119 | 11/1989 | (CA) . |
| 1264751 | 1/1990 | (CA) . |
| 1292693 | 12/1991 | (CA) . |
| 2083605 | 12/1991 | (CA) . |
| 1302891 | 6/1992 | (CA) . |
| 2046364 | 1/1993 | (CA) . |
| 1324758 | 11/1993 | (CA) . |
| 2140347 | 2/1994 | (CA) . |
| 2139653 | 12/1994 | (CA) . |
| 2170647 | 1/1996 | (CA) . |
| 2193681 | 1/1996 | (CA) . |
| 1338377 | 6/1996 | (CA) . |
| 2037101 | 3/1997 | (CA) . |
| 2166794 | 3/1997 | (CA) . |
| 2166483 | 9/1997 | (CA) . |
| 124495 | 7/1984 | (EP) . |
| 0173664 | 3/1986 | (EP) . |
| 1234058 | 6/1971 | (GB) . |
| WO8503436 | 8/1985 | (WO) . |
| WO9501783 | 1/1995 | (WO) . |
| WO9510264 | 4/1995 | (WO) . |
| WO9512590 | 5/1995 | (WO) . |
| WO9601612 | 1/1996 | (WO) . |
| WO9601622 | 1/1996 | (WO) . |
| WO9601623 | 1/1996 | (WO) . |
| WO9602535 | 2/1996 | (WO) . |
| WO9624375 | 8/1996 | (WO) . |

\* cited by examiner

*Primary Examiner*—Thurman K. Page
*Assistant Examiner*—S. Tran
(74) *Attorney, Agent, or Firm*—Hedman, Gibson & Costigan, P.C.

(57) ABSTRACT

A pharmaceutical composition of omeprazole for oral administration is described which consists essentially of:

(a) a tabletted core component containing a therapeutically effective amount of omeprazole, a surface active agent, a filler, a pharmaceutically acceptable alkaline agent and a binder; and (b) a single layer of coating on said core which comprises a layer of an enteric coating agent.

9 Claims, No Drawings

OMEPRAZOLE FORMULATION

BACKGROUND OF THE INVENTION

The present invention relates to a stable formulation of omeprazole. It is well known that omeprazole is sensitive to acidic conditions and after contact with an acid, omeprazole will degrade and will not function in its intended manner. Initially, alkaline materials were added to a core of omeprazole and later an enteric coating was applied over the core to prevent the omeprazole from contacting the acidic pH conditions of the stomach. This approach is satisfactory if the product is administered within a short time after it is manufactured but if the product is stored under ambient conditions, the acidic residue of the enteric coating appears to degrade the omeprazole before it is administered to a patient. To solve this problem, the prior art has used a separate layer of a coating agent to coat a pellet core which contains omeprazole and an alkaline material which is thereafter coated with the enteric coating. This technique is described in U.S. Pat. No. 4,786,505.

This dual layer coating technique requires the application of two separate functional coating operations which increases the length of the manufacturing process and the cost of the product. The applicants have surprisingly discovered a coating system which avoids the need to use a coating layer to separate the omeprazole core from the enteric coating layer in an omeprazole dosage form. The separate coating system is based on the combined use of an enteric coating agent which is applied to cores of omeprazole as a suspension in an suitable solvent.

SUMMARY OF THE INVENTION

The present invention provides a novel dosage form of omeprazole which consists essentially of:
  (a) a compressed tablet core made from a granulation comprising a therapeutically effective amount of omeprazole, a surface active agent, a filler, a pharmaceutically acceptable alkaline agent and a binder; and
  (b) a single layer of coating on said core which comprises a layer of an enteric coating agent.

Accordingly, it is a primary object of this invention to provide a pharmaceutical dosage formulation of omeprazole which is stable upon prolonged storage, is stable when administered to a patient and is capable of providing the desired therapeutic effect.

It is also an object of this invention to provide a pharmaceutical dosage form of omeprazole which is bioequivalent to dosage forms of omeprazole which have an intermediate layer of an inert coating material.

It is also an object of this invention to provide a stable dosage form of omeprazole which may be produced without the need to provide an intermediate coating layer that separates the omeprazole containing core from the enteric coating layer.

These and other objects of the invention will become apparent from a review of the appended specification.

DETAILED DESCRIPTION OF THE INVENTION

The omeprazole formulation of the invention is preferably based on a compressed tablet core formed from granulation which comprises omeprazole, a surface active agent, a filler, an alkaline material and a binder.

The omeprazole may comprise from 5 to 70 wt % and preferably 10 to 30 wt % of the granulation.

The surface active agent may be any pharmaceutically acceptable, non-toxic surfactant. Suitable surface active agents include sodium lauryl sulfate, polysorbate 20, polysorbate 40, polysorbate 60, polysorbate 80 and the like.

The surface active agent may be present at a level of from 0.1 to 5 wt % and preferably 0.20 to 2.0 wt % based on the total weight of the granulation.

The alkaline material is selected from the group consisting of the sodium, potassium, calcium, magnesium and aluminum salts of phosphoric acid, carbonic acid, citric acid and aluminum/magnesium compounds such as $Al_2O_3.6MgO.CO_2.12H_2O$, $(Mg_6Al_2(OH)_{1-6}CO_3.4H_2O)$, $MgO.Al_2O_3.2SiO_2.nH_2O$ where n is a whole integer of 2 or more. In addition the alkaline material may be selected from lysine or arginine or from the group consisting of antacid materials such as aluminum hydroxides, calcium hydroxides, magnesium hydroxides and magnesium oxide. The alkaline agent may be present at a level of 10 to 80 wt % based on the total weight of the granulation, depending on the relative strength of the alkaline material. If the preferred arginine is employed, a level of from 20 to 60 wt % and preferably 30 to 55 wt % based on the weight of the granulation may be employed.

The binder may be any pharmaceutically acceptable, non-toxic pharmaceutically acceptable binder. The binder is preferably a water soluble polymer of the group consisting of polyvinyl alcohol, polyvinylpyrrolidone, methylcellulose, hydroxypropyl cellulose, hydroxymethyl cellulose and the like. A water soluble binder is preferred which is applied from an aqueous medium such as water at a level of from 0.1 to 10 wt % and preferably from 0.25 to 7.5 wt % of binder based on the total weight of the granulation.

A filler is used as a granulation substrate. Sugars such as lactose, dextrose, sucrose, maltose, or microcrystalline cellulose and the like may be used as fillers in the granulation composition. The filler may comprise from 25 to 50 wt % and preferably 20 to 40 wt % based on the total weight of the granulation.

A tablet disintegrant may be added which comprises corn starch, potato starch, croscarmelose sodium, crospovidone and sodium starch glycolate in an effective amount. An effective amount which may be from 3 to 7 wt % based on the total weight of the granulation.

The enteric coating agent may comprise an acid resisting material which resists acid up to a pH of above about 5.0 or higher which is selected from the group consisting of cellulose acetate phthalate, hydroxypropylmethyl cellulose phthalate, polyvinyl acetate phthalate, carboxymethylethylcellulose, Eudragit L (poly(methacrylic acid, methylmethacrylate), 1:1 ratio; MW (No. Av. 135,000—USP Type A) or Eudragit S (poly(methacrylic acid, methylmethacrylate, 1:2 ratio MW (No. Av. 135,000—USP Type B) and mixtures thereof. For example Eudragit L100-55 is a 100% polymer solids product while the Eudragit L30-55 product is a 30% w/w/aqueous dispersion of the polymer. The enteric coating agent may also include an inert processing aid in an amount from 10 to 50 wt % and preferably 20 to 40 wt % based on the total weight of the acid resisting component and the inert processing aid. The inert processing aids include finely divided forms of talc, silicon dioxide, magnesium stearate etc. Typical solvents which may be used to apply the acid resisting component-inert processing aid mixture include isopropyl alcohol, acetone, methylene chloride and the like. Generally the acid resistant component-inert processing aid mixture will be applied from a 5 to 20 wt % of acid resisting component-inert processing aid mixture based on the total weight of the solvent and the acid resistant component-inert processing aid.

The enteric coating may optionally comprise a plasticizer. Suitable plasticizers include acetyl triethyl citrate, dibutyl phthalate, tributyl citrate, triethyl citrate, acetyl tributyl citrate, propylene glycol, triacetin, polyethylene glycol and diethyl phthalate. The amount of plasticizer can vary, but will typically be present in the amount of 0 to 40% w/w based upon the weight acid resisting component of the coating, and more preferably about 10–20% w/w based upon the weight of the acid resisting component.

The granulation is formed by contacting the alkaline agent, the omeprazole, the surface active agent and the binder with a medium which may comprise any low viscosity solvent such as water, isopropyl alcohol, acetone, ethanol or the like. When fluids such as water are employed, this will usually require a weight of fluid which is about three times the weight of the dry components of the coating composition.

After the granulation is formed and dried, the granulation is tabletted and the tablets are directly coated with the enteric coating agent. A color imparting agent may be added to the enteric coating agent mixture or a rapidly dissolving seal coat containing color may be coated over the enteric coating agent layer provided that the seal coat is compatible with and does not affect the dissolution of the enteric coating layer. The rapidly dissolving seal coat may comprise Opadry pink which comprises approximately 91 wt % hydroxypropyl methylcellulose (E-6), color and 9 wt % polyethylene glycol which is applied as a 8–15% w/w solution in purified water. In addition the color may be provided as "Chromateric" which is available from Crompton & Knowles. This product contains water, talc, $TiO_2$, triethyl citrate, propylene glycol, synthetic red iron oxide, potassium sorbate, xanthan gum, sodium citrate and synthetic yellow iron oxide. If desired, conventional sugar based seal coats may be used which contain FDA certified dyes.

DESCRIPTION OF THE PREFERRED EMBODIMENTS

Example 1

Granulation

A granulation containing omeprazole is formed in fluid bed coater using a top spray granulation forming suspension containing micronized omeprazole, 5% w/w of the total amount of L-arginine, polyvinyl pyrrolidone, sodium lauryl sulfate and purified water which is sprayed onto a mixture of microcrystalline cellulose, 95% w/w of the total amount of L-arginine and sodium starch glycolate. The formulation for making the granulation has the following composition:

| | |
|---|---:|
| povidone, USP (Plasdone K30) | 100.0 g |
| sodium starch glycolate | 100.0 g |
| sodium lauryl sulfate, NF/USP | 6.0 g |
| microcrystalline cellulose (AvicelPH101) | 965.6 g |
| L-arginine, USP/FCC | 1020.0 g |
| omeprazole, USP (micronized)[1] | 340.0 g |
| purified water, USP | 1100.0 g |

[1]95% of the particles exhibit a particle size of less than 15 microns

Tabletting

The granulation is tabletted into tablets containing 20 mg of omeprazole by first mixing the omeprazole granules with glyceryl monostearate:

| | |
|---|---:|
| omeprazole granules | 118.0 g |
| glyceryl monostearate (EASTMAN 600P) | 6.0 g |
| Tabletting tools | 0.2812" |
| target weight | 124 mg/tab |
| target hardness | 7Kp |
| LOD of granules | less than 3% |

Enteric Coating

An enteric coating was applied to prepare enteric coated tablets as follows:

| | |
|---|---:|
| omeprazole tablets (prepared above) | 124.0 g |
| hydroxypropyl methylcellulose phthalate 55 | 14.7 g |
| talc | 4.2 g |
| acetyl tributyl citrate | 2.9 g |
| acetone | 148.0 g |
| isopropyl alcohol | 148.0 g |

The solid coating materials were dissolved in the acetone and isopropyl alcohol and this solution was coated onto the omeprazole tablets using a perforated pan.

Seal Coat

A seal coat was applied to the enteric coated tablets as follows:

| | |
|---|---:|
| Enteric coated tablet | 146.0 g |
| Opadry II pink | 4.5 g |
| Water | 450.0 g |

The seal coat was applied onto the enteric coated omeprazole tablets using a perforated pan coater.

Example 2

Granulation

A granulation containing omeprazole is formed in fluid bed coater using a top spray granulation forming suspension containing micronized omeprazole, 5.00% w/w of the total amount of L-arginine, polyvinyl pyrrolidone, polysorbate 80 and purified water which is sprayed onto a mixture of microcrystalline cellulose and 95.0% w/w of the total amount of L-arginine. The formulation for making the granulation has the following composition:

| | mg/tablet |
|---|---:|
| povidone, USP (Plasdone K30) | 5.88 |
| polysorbate 80 (Tween 80) | 0.58 |
| L-arginine, USP/FCC | 60.0 |
| omeprazole, USP (micronized)[2] | 20.0 |
| microcrystalline cellulose (Avicel PH102) | 25.54 |
| purified water, USP | n/a |

[2]95% of the particles exhibit a particle size of less than 15 microns

Tabletting

The granulation is tabletted into tablets containing 20 mg of omeprazole by first mixing the omeprazole granules with crospovidone XL, then with glyceryl monostearate:

| | |
|---|---|
| omeprazole granules | 112.0 mg |
| glyceryl monostearate (EASTMAN 600P) | 6.8 mg |
| crospovidone XL | 16.2 mg |
| Tabletting tools | 0.2812" |
| target weight | 135 mg/tab |
| target hardness | 7Kp |
| LOD of granules | less than 3% |

Enteric Coating

An enteric coating was applied to prepare enteric coated tablets as follows:

| | |
|---|---|
| omeprazole tablets (prepared above) | 135.0 mg |
| Eudragit L30D-55 | 14.0 mg |
| color (Chromateric) | 7.0 mg |
| 1M NaOH (pH adjuster to pH 5.0)qs | na |
| Purified water qs | na |

The solid coating materials were dispersed in the water and this mixture was coated onto the omeprazole tablets using a perforated pan.

Example 3

Granulation

A granulation containing omeprazole is formed in fluid bed coater using a top spray granulation forming suspension containing micronized omeprazole, 5.0% w/w of the total amount of L-arginine, polyvinyl pyrrolidone, sodium lauryl sulfate and purified water which is sprayed onto a mixture of microcrystalline cellulose and 95.0% w/w of the total amount of L-arginine. The formulation for making the granulation has the following composition:

| | mg/tablet |
|---|---|
| povidone, USP (Plasdone K30) | 5.0 |
| sodium lauryl sulfate | 0.3 |
| L-arginine, USP/FCC | 60.0 |
| omeprazole, USP (micronized)[3] | 10.0 |
| microcrystalline cellulose (AvicelPH102) | 24.7 |
| purified water, USP | n/a |

[3]95% of the particles exhibit a particle size of less than 15 microns

Tabletting

The granulation is tabletted into tablets containing 10 mg of omeprazole by first mixing the omeprazole granules with sodium starch glycolatye and then with glyceryl monostearate:

| | |
|---|---|
| omeprazole granules | 100.0 mg |
| glyceryl monostearate (EASTMAN 600P) | 5.0 mg |
| sodium starch glycolate | 5.0 mg |
| Tabletting tools | 0.2812" |
| target weight | 110 mg/tab |
| target hardness | 7Kp |
| LOD of granules | less than 3% |

Enteric Coating

The tablets were coated with the same enteric coating that was applied to the tablets in Example 2.

Example 4

Granulation

A granulation containing omeprazole is formed in fluid bed coater using a top spray granulation forming suspension containing micronized omeprazole, 5.0% w/w of the total amount of L-arginine, polyvinyl pyrrolidone, sodium lauryl sulfate and purified water which is sprayed onto a mixture of microcrystalline cellulose, crospovidone XL and 95.0% w/w of the total amount of L-arginine. The formulation for making the granulation has the following composition:

| | mg/tablet |
|---|---|
| povidone, USP (Plasdone K30) | 5.88 |
| polysorbate 80 | 0.60 |
| L-arginine, USP/FCC | 60.0 |
| omeprazole, USP (micronized)[4] | 20.0 |
| crospovidone XL | 5.88 |
| microcrystalline cellulose | 25.54 |
| purified water, USP | n/a |

[4]95% of the particles exhibit a particle size of less than 15 microns

Tabletting

The granulation is tabletted into tablets containing 20 mg of omeprazole by first mixing the omeprazole granules with glyceryl monostearate:

| | |
|---|---|
| omeprazole granules | 117.9 mg |
| glyceryl monostearate (EASTMAN 600P) | 6.1 mg |
| Tabletting tools | 0.2812" |
| target weight | 124 mg/tab |
| target hardness | 7Kp |
| LOD of granules | less than 3% |

Enteric Coating

The tablets were coated with the same enteric coating that was applied to the tablets in Example 1.

Example 5

The granulation of Example 1 was prepared and tabletted into tablets containing 20.0 mg of omeprazole. These tablets were coated as follows:

Enteric Coating

An enteric coating was applied to prepare enteric coated tablets as follows:

| | |
|---|---|
| omeprazole tablets (prepared above) | 126.00 mg |
| Eudragit L30D-55 | 17.00 mg |
| 1M NaOH (pH adjuster to pH 5.0)qs | na |
| acetyl tributyl citrate | 1.70 mg |
| talc | 3.80 mg |
| polysorbate 80 | 1.50 mg |
| purified water qs | na |

The coating polymer was diluted with water and the other coating materials were added. This mixture was coated onto the omeprazole tablets using a perforated pan. A seal coat was applied using the procedure of Example 1.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A stable pharmaceutical dosage formulation for oral administration consisting essentially of:
   (a) a tabletted core consisting essentially of 5 to 70 weight percent based on the total weight of the core of omeprazole, 0.1 to 5 weight percent based on the total weight of the core of a surface active agent, 25 to 50 weight percent based on the total weight of the core of a filler, 0.1 to 10 weight percent based on the total weight of the core of a binder and 20 to 60 weight percent based on the total weight of the core of a pharmaceutically acceptable alkaline agent, wherein the alkaline agent is selected from the group consisting of lysine and arginine; and
   (b) a coating layer surrounding the core that consists of an enteric coating agent, 10 to 50 weight percent based on the total weight of the coating layer of an inert processing aid and 0 to 40 weight percent based on the total weight of the coating layer of a plasticizer wherein the coating layer is applied directly to the omeprazole containing core without a separating layer between the omeprazole containing core and coating layer.

2. A pharmaceutical composition of omeprazole as defined in claim 1, wherein the alkaline agent is arginine.

3. A pharmaceutical composition of omeprazole as defined in claim 1, wherein the enteric coating agent is selected from the group consisting of cellulose acetate phthalate, hydroxypropylmethyl cellulose phthalate, polyvinyl acetate phthalate, carboxymethylethylcellulose, co-polymerized methacrylic acid/methacrylic acid methyl esters.

4. A pharmaceutical composition of omeprazole as defined in claim 1 which includes a sodium lauryl sulfate as the surface active agent.

5. A method for preparing a stable oral pharmaceutical dosage formulation which consists essentially of:
   (a) forming a tablet core consisting essentially of 5 to 70 weight percent based on the total weight of the core of omeprazole, 0.1 to 10 weight percent based on the total weight of the core of a binder, 25 to 50 weight percent based on the total weight of the core of a filler, 0.1 to 5 weight percent based on the total weight percent of the core of a surface active agent and 20–60 weight percent based on the total weight of the core of an alkaline agent wherein the alkaline agent is selected from the group consisting of lysine and arginine; and
   (b) applying a coating layer to the tablet core that surrounds the tablet core and consists of an enteric coating agent, 10 to 50 weight percent based on the total weight of the coating layer of an inert processing aid and 0 to 40 weight percent based on the total weight of the coating layer of a plasticizer wherein the coating layer is applied directly to the omeprazole containing tablet core without a separating layer between the omeprazole containing tablet core and coating layer.

6. The dosage formulation as defined in claim 1 wherein the core consists essentially of 10 to 30 weight percent based upon the total weight of the core of omeprazole; 0.20 to 2.0 weight percent based upon the total weight of the core of the surface active agent; 0.25 to 7.5 weight percent based upon the total weight of the core of the binder; 20 to 40 weight percent based upon the total weight of the core of the filler and 30–55 weight percent based upon the total weight of the core of the alkaline agent.

7. The dosage formulation as defined in claim 1 wherein the coating layer consists of 20 to 40 weight percent based upon the total weight of the coating layer of the inert processing aid and 10 to 20 weight percent based upon the total weight of the coating layer of the plasticizer.

8. The method as defined in claim 5 wherein the core consists essentially of 10 to 30 weight percent based upon the total weight of the core of omeprazole; 0.20 to 2.0 weight percent based upon the total weight of the core of the surface active agent; 0.25 to 7.5 weight percent based upon the total weight of the core of the binder; 20 to 40 weight percent based upon the total weight of the core of the filler and 30–55 weight percent based upon the total weight of the core of the alkaline agent.

9. The method as defined in claim 5 wherein the coating layer consists of 20 to 40 weight percent based upon the total weight of the coating layer of the inert processing aid and 10 to 20 weight percent based upon the total weight of the coating layer of the plasticizer.

* * * * *